United States Patent [19]
Drucker

[11] Patent Number: 5,990,077
[45] Date of Patent: *Nov. 23, 1999

[54] GLUCAGON-LIKE PEPTIDE-2 AND ITS THERAPEUTIC USE

[75] Inventor: Daniel J. Drucker, Toronto, Canada

[73] Assignee: 1149336 Ontario Inc., Toronto, Canada

[ * ] Notice: This patent is subject to a terminal disclaimer.

[21] Appl. No.: 08/422,540

[22] Filed: Apr. 14, 1995

[51] Int. Cl.⁶ .................................................... A61K 38/00
[52] U.S. Cl. ................................... 514/2; 514/3; 514/12; 530/303; 530/308; 530/324
[58] Field of Search ...................... 514/2, 3, 12; 530/324, 530/308, 303; 935/52, 55, 66, 70, 71; 435/366, 371

[56] References Cited

FOREIGN PATENT DOCUMENTS 612531 8/1994 European Pat. Off. .

OTHER PUBLICATIONS

Barragan, J.M.; Rodriguez, R.E.; and Blazquez, E. Changes in arterial blood pressure and heart rate induced by glucagon–like peptide–1–(7–36) amide in rats. *American Journal of Physiology*. 266 (3 Pt 1), pE459–66, Mar. 1994.
Bloom, S.R. Gut Hormones in adaptation. *Gut*. 28, S1, pp. 31–35, 1987.
Brubaker, Patricia L. Regulation of Intestinal Proglucagon–Derived Peptide Secretion by Intestinal Regulatory Peptides. *Endocrinology*. vol. 128, No. 6, pp. 3175–3182, 1991.
Buhl, Thora; Thim, Lars; Kofod, Hans; Orskov, Catherine; Harling, Henrik; and Holst, Jens J. Naturally Occurring Products of Proglucagon 111–160 in the Porcine and Human Small Intestine. *The Journal of Biological Chemsitry*. vol. 263, No. 18, pp. 8621–8624, Issue of Jun. 25, 1988.
Calvo, J.C.; Yusta, B; Mora, F; and Blazquez, E. Structural characterization by affinity cross–linking of glucagon–like peptide–1 (7–36) amide receptor in rat brain. *J. Neurochem.* 64(1), pp. 299–306, Jan. 1995.
Cheeseman, Chris I.; and Raymand Tsang. The effect of gastric inhibitory polypeptide and glucagon like peptides on intestinal basolateral membrane hexose transport. *The American Physiological Society*. APSracts 3:0071G, Apr. 16, 1996.
Drucker. *Pancreas*. 1990, 5(4):484.
Ehrlich, Peter; Tucker, Devin; Asa, Sylvia L.; Brubacker, Patricia L.; and Drucker, Daniel J. Inhibition of pancreatic proglucagon gene expression in mice bearing subcutaneous endocrine tumors. *American Journal of Physiology*. pp. E662–E671, 1994.
George, S.K.; Uttenthal, L.O.; Ghiglione, M.; and Bloom, S.R. Molecular forms of glucagon–like peptides in man. *FEBS Letters*. vol. 192, No. 2, pp. 275–278, Nov. 1985.
Hoosein, Naseema M.; and Gurd, Ruth S. Human glucagon–like peptides 1 and 2 activate rat brain adenylate cyclase. *FEBS Letters*. vol. 178, No. 1, pp. 83–86, Dec. 1984.
Irwin, David M.; and Wong, Jaffe. Trout and Chicken Proglucagon: Alternative Splicing Generates mRNA Transcripts Encoding Glucagon–Like Peptide 2. *Molecular Endocrinology*. 9:267–277, 1995.

Lee, Ying C.; Asa, Sylvia L.; and Drucker, Daniel J. Glucagon Gene 5'–Flanking Sequences Direct Expression of Simian Virus 40 Large T Antigen to the Intestine, Producing Carcimona of the Large Bowel in Transgenic Mice. *The Journal of Biological Chemistry*. vol. 267, No. 15, pp. 10706–10708, May 25, 1992.
Lund, P. Kay; Hoyt, Eileen; Simmons, James G.; and Ulshen, Martin H. Regulation of Intestinal Glucagon Gene Expression during Adaptive Growth of Small Intestine. *Digestion*. 54:371–373. 1993.
Mojsov, Svetlana; Heinrich, Gerhard; Wilson, Ira B.; Ravazzola, Mariella; Orci, Lelio; and Habener, Joel F. Preproglucagon Gene Expression in Pancreas and Intestine Diversifies at the Level of Post–translational Processing. *The Journal of Biological Chemistry*. vol. 261, No. 25, pp. 11880–11889, Sep. 5, 1986.
Mommsen, Thomas P.; Andrews, P.C.; and Plisetskaya, Erika M. Glucagon–like peptides activate hepatic gluconeogenesis. *FEBS Letters*. vol. 219, No. 1, pp. 227–232, Jul. 1987.
Nishi and Steiner, *Mol. Endocrinol.*, 1990, 4:1192–8.
Orskov, C.; Buhl, T.; Rabenhoj, L.; Kofod, H.; and Holst, J.J.. Carboxypeptidase–B–like processing of the C–terminus of glucagon–like peptide–2 in pig and human small intestine. *FEBS Letters*. 247(2), pp. 193–196, Apr. 24, 1989.
Orskov, C.; Holst, J.J.; Pouisen, S. Seier; and Kirkegaard, P. Pancreatic and intestinal processing of proglucagon in man. *Diabetologia*. 30:874–881, 1987.
Orskov, C; and Holst, J.J. Radio–immunoassays for glucagon–like peptides 1 and 2 (GLP–1 and GLP–2). *Scand. J. Clin. Lab. Invest.* 47(2), pp. 165–174, Apr. 1987.
Orskov, Catherine; Holst, Jens J.; Khuhtsen, Svend; Baldissera, Furio G.A.; Poulsen, Steen S.; and Nielsen, O. Vagn. Glucagon–Like Peptides GLP–1 and GLP–2, Predicted Products of the Glucagon Gene, Are Secreted Separately from Pig Small Intestine but Not Pancreas. *Endocrinology*. vol. 119, No. 4, pp. 1467–1475, 1986.
Ruiz–Grand, C.; Pintado, J.; Alarcon, C.; Castilla, C.; Valverde, I; Lopez–Novoa, J.M. Renal catabolism of human glucagon–like peptides 1 and 2. *Can. J. Physiol. Pharmacol.* 68(12), pp. 1568–1573, Dec. 1990.
Shennan, K.I.J.; Holst, J.J.; and Docherty, K. Proglucagon expression, posttranslational processing and secretion in SV40–transformed islet cells. *Molecular and Cellular Endocrinology*. 67(1989), pp. 93–99.
Watanabe, Nobuaki; Matsuyama, Tatsuo; Namba, Mitsuyoshi; Miyagawa, Jun–ichiro; Itoh, Hidehiko; Komatsu, Ryoya; Kono, Norio; and Tarui, Seiichiro. Trophic Effect of Glucagon–(1–21)–Peptide on the Isolated Rat Ileal Mucosal Cells. *Biochemical and Biophysical Research Communications*. vol. 152, No. 3, pp. 1038–1044, May 16, 1988.

*Primary Examiner*—Sheela Huff
*Attorney, Agent, or Firm*—Pennie & Edmonds LLP

[57] ABSTRACT

Glucagon-like peptide 2, a product of glucagon gene expression, has been identified as a gastrointestinal tissue growth factor. Its effects on the growth of small intestine and on pancreatic islets are described. Its formulation as a pharmaceutical, and its therapeutic use in treating bowel tissue disorders and in treating diabetes, are described.

80 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 37 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified Base
       (B) LOCATION: 1
       (D) OTHER INFORMATION: /note=Xaa is Arg and may or may not be
                             present
       (A) NAME/KEY: Modified Base
       (B) LOCATION: 2
       (D) OTHER INFORMATION: /note=Xaa is Arg and may or may not be
                             present
       (A) NAME/KEY: Modified Base
       (B) LOCATION: 15
       (D) OTHER INFORMATION: /note=Xaa is a neutral/polar/large/
                             nonaromatic residue such as Ile or Val
       (A) NAME/KEY: Modified Base
       (B) LOCATION: 18
       (D) OTHER INFORMATION: /note=Xaa is a neutral/polar residue
                             such as Asn or Ser
       (A) NAME/KEY: Modified Base
       (B) LOCATION: 21
       (D) OTHER INFORMATION: /note=Xaa is a neutral residue such as
                             Ala or Thr
       (A) NAME/KEY: Modified Base
       (B) LOCATION: 29
       (D) OTHER INFORMATION: /note=Xaa is a neutral/polar/large/
                             nonaromatic residue such as Ile or Leu
       (A) NAME/KEY: Modified Base
       (B) LOCATION: 30
       (D) OTHER INFORMATION: /note=Xaa is a neutral or basic residue
                             such as Gln or His
       (A) NAME/KEY: Modified Base
       (B) LOCATION: 36
       (D) OTHER INFORMATION: /note=Xaa is Arg or Lys and may or may
                             not be present
       (A) NAME/KEY: Modified Base
       (B) LOCATION: 37
       (D) OTHER INFORMATION: /note=Xaa is Lys and may or may not be
          present (xi) SEQUENCE DESCRIPTION: SEQ ID NO:1:

Xaa Xaa His Ala Asp Gly Ser Phe Ser Asp Glu Met Asn Thr Xaa Leu
 1               5                  10                  15

Asp Xaa Leu Ala Xaa Arg Asp Phe Ile Asn Trp Leu Xaa Xaa Thr Lys
            20                  25                  30

Ile Thr Asp Xaa Xaa
        35

(2) INFORMATION FOR SEQ ID NO:2:

(i) SEQUENCE CHARACTERISTICS:
       (A) LENGTH: 37 amino acids
       (B) TYPE: amino acid
       (C) STRANDEDNESS:
       (D) TOPOLOGY: unknown (ii) MOLECULE TYPE: peptide (ix) FEATURE:
       (A) NAME/KEY: Modified Base (B) LOCATION: 1
              (D) OTHER INFORMATION: /note=Xaa is Arg and may or may not be
                           be present
              (A) NAME/KEY: Modified Base
              (B) LOCATION: 2
              (D) OTHER INFORMATION: /note=Xaa is Arg and may or may not be
                           be present
              (A) NAME/KEY: Modified Base
              (B) LOCATION: 21
              (D) OTHER INFORMATION: /note=Xaa is a neutral residue such as
                           Ala or Thr
              (A) NAME/KEY: Modified Base
              (B) LOCATION: 36
              (D) OTHER INFORMATION: /note=Xaa is Arg or Lys and may or may
                           not be present
              (A) NAME/KEY: Modified Base
              (B) LOCATION: 37
              (D) OTHER INFORMATION: /note=Xaa is Lys and may or may not be
                           present (xi) SEQUENCE DESCRIPTION: SEQ ID NO:2:

Xaa Xaa His Ala Asp Gly Ser Phe Ser Asp Glu Met Asn Thr Ile Leu
             5                  10                  15

Asp Asn Leu Ala Xaa Arg Asp Phe Ile Asn Trp Leu Ile Gln Thr Lys
             20                  25                  30

Ile Thr Asp Xaa Xaa
             35

(2) INFORMATION FOR SEQ ID NO:3:

(i) SEQUENCE CHARACTERISTICS:
        (A) LENGTH: 33 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:3:

His Ala Asp Gly Ser Phe Ser Asp Glu Met Asn Thr Ile Leu Asp Asn
 1               5                  10                  15

Leu Ala Thr Arg Asp Phe Ile Asn Trp Leu Ile Gln Thr Lys Ile Thr
             20                  25                  30

Asp (2) INFORMATION FOR SEQ ID NO:4:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
         (A) NAME/KEY: Modified Base
         (B) LOCATION: 1
         (D) OTHER INFORMATION: /note=Xaa is Arg and may or may not be
                      present
         (A) NAME/KEY: Modified Base
         (B) LOCATION: 2
         (D) OTHER INFORMATION: /note=Xaa is Arg and may or may not be
                      present
         (A) NAME/KEY: Modified Base
         (B) LOCATION: 15
         (D) OTHER INFORMATION: /note=Xaa is a neutral/polar/large/
                      nonaromatic amino acid residue
         (A) NAME/KEY: Modified Base
         (B) LOCATION: 18
         (D) OTHER INFORMATION: /note=Xaa is a neutral/polar amino
                      acid residue (A) NAME/KEY: Modified Base
            (B) LOCATION: 21
            (D) OTHER INFORMATION: /note=Xaa is a neutral amino acid
                        residue
            (A) NAME/KEY: Modified Base
            (B) LOCATION: 29
            (D) OTHER INFORMATION: /note=Xaa is a neutral/polar/large/
                        nonaromatic amino acid residue
            (A) NAME/KEY: Modified Base
            (B) LOCATION: 30
            (D) OTHER INFORMATION: /note=Xaa is a neutral or basic amino
                        acid residue
            (A) NAME/KEY: Modified Base
            (B) LOCATION: 36
            (D) OTHER INFORMATION: /note=Xaa is Arg or Lys and may or may
                        not be present
            (A) NAME/KEY: Modified Base
            (B) LOCATION: 37
            (D) OTHER INFORMATION: /note=Xaa is Lys and may or may not be
                present (xi) SEQUENCE DESCRIPTION: SEQ ID NO:4:

Xaa Xaa His Ala Asp Gly Ser Phe Ser Asp Glu Met Asn Thr Xaa Leu
  1               5                  10                  15

Asp Xaa Leu Ala Xaa Arg Asp Phe Ile Asn Trp Leu Xaa Xaa Thr Lys
             20                  25                  30

Ile Thr Asp Xaa Xaa
            35

(2) INFORMATION FOR SEQ ID NO:5:

(i) SEQUENCE CHARACTERISTICS:
            (A) LENGTH: 37 amino acids
            (B) TYPE: amino acid
            (C) STRANDEDNESS:
            (D) TOPOLOGY: unknown (ii) MOLECULE TYPE: peptide (ix) FEATURE:
            (A) NAME/KEY: Modified Base
            (B) LOCATION: 1
            (D) OTHER INFORMATION: /note=Xaa is Arg and may or may not be
                    present
            (A) NAME/KEY: Modified Base
            (B) LOCATION: 2
            (D) OTHER INFORMATION: /note=Xaa is Arg and may or may not be
                    present
            (A) NAME/KEY: Modified Base
            (B) LOCATION: 15
            (D) OTHER INFORMATION: /note=Xaa is Ile or Val
            (A) NAME/KEY: Modified Base
            (B) LOCATION: 18
            (D) OTHER INFORMATION: /note=Xaa is a neutral/polar amino
                            acid residue
            (A) NAME/KEY: Modified Base
            (B) LOCATION: 21
            (D) OTHER INFORMATION: /note=Xaa is a neutral amino acid
                        residue
            (A) NAME/KEY: Modified Base
            (B) LOCATION: 29
            (D) OTHER INFORMATION: /note=Xaa is a neutral/polar/large/
                            nonaromatic
                amino acid residue
            (A) NAME/KEY: Modified Base
            (B) LOCATION: 30
            (D) OTHER INFORMATION: /note=Xaa is a neutral or basic amino
                        acid residue
            (A) NAME/KEY: Modified Base
            (B) LOCATION: 36
            (D) OTHER INFORMATION: /note=Xaa is Arg or Lys and may or may
                        not be present
            (A) NAME/KEY: Modified Base
            (B) LOCATION: 37
            (D) OTHER INFORMATION: /note=Xaa is Lys and may or may not be
                        present (xi) SEQUENCE DESCRIPTION: SEQ ID NO:5:

Xaa Xaa His Ala Asp Gly Ser Phe Ser Asp Glu Met Asn Thr Xaa Leu
 1               5                  10                  15

Asp Xaa Leu Ala Xaa Arg Asp Phe Ile Asn Trp Leu Xaa Xaa Thr Lys
                20                  25                  30

Ile Thr Asp Xaa Xaa
            35

(2) INFORMATION FOR SEQ ID NO:6:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified Base
        (B) LOCATION: 1
        (D) OTHER INFORMATION: /note=Xaa is Arg and may or may not be
                               present
        (A) NAME/KEY: Modified Base
        (B) LOCATION: 2
        (D) OTHER INFORMATION: /note=Xaa is Arg and may or may not be
                               present
        (A) NAME/KEY: Modified Base
        (B) LOCATION: 21
        (D) OTHER INFORMATION: /note=Xaa is a neutral amino acid
                               residue
        (A) NAME/KEY: Modified Base
        (B) LOCATION: 36
        (D) OTHER INFORMATION: /note=Xaa is Arg or Lys and may or
                               may not be present
        (A) NAME/KEY: Modified Base
        (B) LOCATION: 37
        (D) OTHER INFORMATION: /note=Xaa is Lys and may or may not be
                               present (xi) SEQUENCE DESCRIPTION: SEQ ID NO:6:

Xaa Xaa His Ala Asp Gly Ser Phe Ser Asp Glu Met Asn Thr Ile Leu
             5                  10                  15

Asp Asn Leu Ala Xaa Arg Asp Phe Ile Asn Trp Leu Ile Gln Thr Lys
                20                  25                  30

Ile Thr Asp Xaa Xaa
            35

(2) INFORMATION FOR SEQ ID NO:7:

(i) SEQUENCE CHARACTERISTICS:
        (A) LENGTH: 37 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Modified Base
        (B) LOCATION: 1
        (D) OTHER INFORMATION: /note=Xaa is Arg and may or may not be
                               present
        (A) NAME/KEY: Modified Base
        (B) LOCATION: 2
        (D) OTHER INFORMATION: /note=Xaa is Arg and may or may not be
                               present
        (A) NAME/KEY: Modified Base
        (B) LOCATION: 21
        (D) OTHER INFORMATION: /note=Xaa is Ala or Thr
        (A) NAME/KEY: Modified Base

```
        (B) LOCATION: 36
        (D) OTHER INFORMATION: /note=Xaa is Arg or Lys and may or may
                                    not be present
        (A) NAME/KEY: Modified Base
        (B) LOCATION: 37
        (D) OTHER INFORMATION: /note=Xaa is Lys and may or may not be
                                    present (xi) SEQUENCE DESCRIPTION: SEQ ID NO:7:

Xaa Xaa His Ala Asp Gly Ser Phe Ser Asp Glu Met Asn Thr Ile Leu
             5                   10                  15

Asp Asn Leu Ala Xaa Arg Asp Phe Ile Asn Trp Leu Ile Gln Thr Lys
            20                  25                  30

Ile Thr Asp Xaa Xaa
            35
```

GLUCAGON-LIKE PEPTIDE-2 AND ITS THERAPEUTIC USE

FIELD OF THE INVENTION

This invention relates to glucagon-related peptides having gastrointestinal tissue growth promoting properties and to their use therapeutically to treat various medical conditions resulting from the impaired growth or loss of tissue, particularly pancreatic and intestinal tissue.

BACKGROUND OF THE INVENTION

Expression of the glucagon gene yields a tissue-determined variety of peptide products that are processed from the 160 residue proglucagon product. The organization of these peptides within the proglucagon precursor was elucidated by the molecular cloning of preproglucagon cDNAs from the anglerfish, rat, hamster and bovine pancreas. These analyses revealed that prepreglucagon contains not only the sequence of glucagon and glicentin, but also two additional glucagon-like peptides (GLP-I and GLP-2) separated from glucagon and each other by two spacer or intervening peptides (IP-I and IP-II). These peptides are flanked by pairs of basic amino acids, chaacteristic of classic prohormone cleavage sites, suggesting they might be liberated after posttranslational processing of proglucagon (Drucker, Pancreas, 1990, 5(4):484).

Analysis of the peptices liberated from proglucagon in the pancreatic islets of Langerhans, for instance, suggests the primary pancreatic peptide liberted is the 29-mer glucagon, whereas glicentin, oxyntomodulin, IP-II and the glucagon-like peptides are more prevalent in the small and large intestines. This demonstration that the glucagon-like peptides are found in the intestine has prompted research into the precise structure and putative function(s) of these newly discovered gut peptides. Most studies have focussed on GLP-I, because several lines of evidence suggested that GLP-I may be an important new regulatory peptide. Indeed, it has been determined that GLP-I is the most potent known peptidergic stimulus for insulin release, an action mediated in a glucose-dependent manner through interaction with receptors on pancreatic β cells. GLP-T and its derivatives are in development for use in the treatment of diabetics.

The physiological roles of glicentin and oxyntomodulin, the so-called "enteroglucagons", are also under investigation, particularly with respect to regulation of acid secretion and the growth of intestinal cells. Oxyntomodulin is capable of inhibiting pentagastrin-stimulated gastric acid secretion in a dose-dependent manner. The role of glicentin in mediating the changes of intestinal adaptation and growth of the intestinal mucosa has been investigated, and the intestinotrophic effect of glicentin and its therapeutic use have recently been reported by Matsuno et al in EP 612,531 published Aug. 31, 1994.

In contrast to GLP-I and other glucagon peptides, the physiological role of glucagon-related peptide GLP-2 remains poorly understood despite the isolation and sequencing of various GLP-2 homologues including human, rat, bovine, porcine, guinea pig, hamster and anglerfish. Using GLP-2 antisera raised against synthetic versions of GLP-2, various groups have determined that GLP-2 is present primarily in intestinal rather than pancreatic extracts (see Mojsov et al, J. Biol. Chem., 1986, 261(25):11880; Orskov et al in Endocrinology, 1986, 119(4):1467 and in Diabetologia, 1987, 30:874 and in FEBS Letters, 1989, 247(2):193; George et al, FEBS Letters, 1985, 192(2):275). With respect to its biological role, Hoosein et al report (FEBS Letters, 1984, 178(1):83) that GLP-2 neither competes with glucagon for binding to rat liver and brain tissues, nor stimulates adenylate cyclase production in liver plasma membranes, but, enigmatically, can stimulate adenylate cyclase in both rat hyopthalamic and pituitary tissue, at 30–50 pM concentrations. An elucidation of the physiological role of GLP-2 would clearly be desirable.

SUMMARY OF THE INVENTION

It has now been determined that GLP-2 acts as a trophic agent to promote growth of gastrointestinal tissue. The effect of GLP-2 is marked particularly by increased growth of the small intestine. Remarkably, the growth promoting effects of GLP-2 are also marked by pancreatic islet growth, and particularly by enlargement and proliferation of the islets. It is accordingly a general object of the present invention to exploit GLP-2 for therapeutic and related purposes.

More particularly, and according to one aspect of the invention, there is provided GLP-2 in a pharmaceutically acceptable form that is suitable for formulation and subsequent administration to patients.

In another of its aspects, the invention provides a pharmaceutical composition comprising GLP-2 and a pharmaceutically acceptable carrier.

In a further aspect, the invention provides a method for promoting the growth of gastrointestinal tissue in a patient in need thereof, comprising the step of delivering to the patient a gastrointestinal tissue growth-promoting amount of GLP-2.

In another aspect of the invention, there is provided a method in which treatment of patients to restore gastrointestinal tissue is performed by the steps of (1) culturing said tissue or cells therefrom with a tissue growth promoting amount of GLP-2, and then (2) implanting the said tissue or cells in the patient to be treated.

In a related aspect, the invention provides a method for growing gastrointestinal tissue or cells therefrom, which comprises the step of culturing the said tissue or cells in a culturing medium supplemented with a growth promoting amount of GLP-2.

DETAILED DESCRIPTION OF THE INVENTION

The invention relates to therapeutic and related uses of GLP-2, particularly for promoting the growth of gastrointestinal tissue, most particularly small intestine or pancreatic islets. With respect to small intestine tissue, such growth is revealed by a GLP-2-mediated increase in small intestine mass, relative to an untreated control. With respect to pancreatic islets, such growth is revealed by GLP-2-mediated enlargement and/or proliferation of pancreatic islets, relative to an untreated control. A model suitable for determining such growth is described by Matsuno et al, supra, and is exemplified herein.

Unless otherwise specified, the term GLP-2 refers collectively herein to the various naturally produced forms of GLP-2, particularly the mammalian forms, e.g., rat GLP2, ox GLP-2, porcine GLP-2, bovine GLP-2, guinea pig GLP-2, hamster GLP-2 and human GLP-2, the sequences of which have been reported by many authors including Buhl et al in J. Biol. Chem., 1988, 263(18):8621. Taking into account the significant sequence homology among these GLP-2 species, the present invention embraces the use, as a gastrointestinal growth promoting factor, of those forms of GLP-2 and the pharmaceutically acceptable acid salts thereof, that conform to the general formula represented below as SEQ ID NO:1

R1-[Y]m-His-Ala-Asp-Gly-Ser-Phe-Ser-Asp-Glu-Met-Asn-Thr-aa1-Leu-Ala-aa2-Leu-Ala-aa3-Arg-Asp-Phe-Ile-Asn-Trp-Leu-aa4-aa5-Thr-Lys-Ile-Thr-Asp-[X]-n-R2 wherein aa refers to an amino acid residue that is synthetic or genetically encoded, and;

aa1 is a neutral/polar/large/nonaromatic residue such as Ile or Val;

aa2 is a neutral/polar residue such as Asn or Ser;

aa3 is a neutral residue such as Ala or Thr;

aa4 is a neutral/polar/large/nonaromatic residue such as Ile or Leu;

aa5 is a neutral or basic residue such as Gln or His;

X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group SEQ ID NO:1.

In particular embodiments of the invention, the GLP-2 conforms to SEQ ID NO:2 shown below:

R1-[Y ]-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 wherein aa3, X, n, R1 and R2 are as defined above SEQ ID NO:2.

In a specific embodiment of the invention, GLP-2 has SEQ ID NO:3 illustrated below:

His-Ala-Asp-Gly-Ser-Phe-Ser-Asp-Glu-Met-Asn-Thr-Ile-Leu-Asp-Asn-Leu-Ala-Thr-Arg-Asp-Phe-Ile-Asn-Trp-Leu-Ile-Gln-Thr-Lys-Ile-Thr-Asp, SEQ ID No:3

The "blocking groups" represented by R1 and R2 are chemical groups that are routinely used to confer biochemical stability and resistance to digestion by exopeptidase. Suitable N-terminal protecting, groups include, for example, $C_{1-5}$alkanoyl groups such as acetyl. Also suitable as N-terminal protecting groups are amino acid analogues lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$alkyl groups, e.g. methyl, ethyl and propyl groups, while amide-forming groups include amino functions such as primary amine, or alkylamino functions, e.g. mono-$C_{1-5}$-alkylamino and di-$C_{1-5}$alkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine.

The particular form of GLP-2 selected for promoting the growth of gastrointestinal tissue can be prepared by a variety of techniques well known for generating peptide products. Those forms of GLP-2 that occur naturally can of course be obtained by extraction from the natural source, using an appropriate combination of protein isolation techniques. As described by Buhl et al, supra, porcine GLP-2 isolation and purification is achieved from acid-ethanol extracts of ileal mucosa by a combination of size selection and HPLC-based fractionation, with the aid of antibody raised against synthetic proglucagon 126–159, to monitor work-up. As an alternative to GLP-2 extraction, those forms of GLP-2 that incorporate only L-amino acids can be produced reproducibly and in commercial quantities by application of recombinant DNA technology. For this purpose, DNA coding for the desired form of GLP-2 is incorporated expressibly in a microbial e.g. yeast, or other cellular host, which is then cultured under conditions appropriate for GLP-2 expression. A variety of gene expression systems have been adapted for this purpose, and typically drive expression of the desired gene from expression controls used naturally by the chosen host. Because GLP-2 does not require post translational glycosylation for its activity, its production may most conveniently be achieved in bacterial hosts such as *E. coli*. For such production, DNA coding for the selected GLP-2 may usefully be placed under expression controls of the lac, trp or PL genes of *E. coli*. As an alternative to expression of DNA coding for the GLP-2 per se, the host can be adapted to express GLP-2 as a fusion protein it which the GLP-2 is linked releasably to a carrier protein that facilitates isolation and stability of the expression product.

In an approach universally applicable to the production of a selected GLP-2, and one used necessarily to produce GLP-2 forms that incorporate non-genetically encoded amino acids and N- and C-terminally derivatized forms, the-well established techniques of automated peptide synthesis are employed, general descriptions of which appear, for example, in J. M. Stewart and J. D. Young, *Solid Phase Peptide Synthesis*, 2nd Edition, 1984, Pierce Chemical Company, Rockford, Ill.; and in M. Bodanszky and A. Bodanszky, *The Practice of Peptide Synthesis*, 1984, Springer-Verlag, New York; Applied Biosystems 430A Users Manual, 1987, ABI Inc., Foster City, Calif. In these techniques, the GLP-2 is grown from its C-terminal, resin-conjugated residue by the sequential addition of appropriately protected amino acids, using either the Fmoc or tBoc protocols, as described for instance by Orskov et al, 1989, supra.

For the incorporation of N- and/or C-protecting groups protocols is conventional to solid phase peptide synthesis methods can also be applied. For incorporation of C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydrylamine, (MBHA) resin so that, when peptide synthesis is completed, treatment with hydrofluoric acid releases the desired C-terminally amidated peptide. Similarly, incorporation of an N-methylamine protecting group at the C-terminus is achieved using N methylaminoethyl-derivatized DVB resin, which upon HF treatment releases peptide baring an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxybenzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence, Purification can be achieved using any of the standard approaches, which include reversed-phase high-pressure liquid chromatography (RP-HPLC) on alkylated silica columns, e.g. $C_4$-, $C_8$-, or $C_{18}$~silica. Such column fractionation is generally accomplished by running linear gradients, e.g. 10–90%, of increasing % organic solvent, e.g. acetonitrile, in aqueous buffer, usually containing a small amount (e.g. 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the peptide is then treated in the established manner to exchange the cleavage acid (e.g. TFA) with a pharmaceutically acceptable acid, such as acetic, hydrochloric, phosphoric, maleic, tartaric, succinic and the likes to provide a water soluble salt of the peptide.

For administration to patients, the GLP-2 is provided, in one aspect of the invention, in pharmaceutically acceptable form, e.g., as a preparation that is sterile-filtered e.g. through a $0.22\mu$ filter, and substantially pyrogen-free. Desirably, the GLP-2 to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to "Remington s Pharmaceutical Sciences", 17th Ed., Mack Publishing Company, Easton, Pa., 1995, for guidance on drug formulations generally. In one embodiment of the invention the compounds are formulated for administration by infusion or by injection, either sub-cutaneously or intravenously, and are accordingly utilized as aqueous solutions in sterile and pyrogen-free form and optionally buffered to a slightly acidic or physiological pH. Thus, the compounds may be administered in distilled water or, more desirably, in saline, buffered saline or 5% dextrose solution. Water solubility of these and other the GLP-2 may be enhanced, if desired, by incorporating a solubility enhancer, such as acetic acid.

For use in stimulating bowel growth in a mammal including a human, the present invention provides in one of its aspects a package, in the form of a sterile-filled vial or ampoule, that contains a tissue growth promoting amount of the GLP-2, in either unit dose or multi-dose amounts, wherein the package incorporates a label instructing use of its contents for the promotion of gastrointestinal tissue growth, e.g. for promotion of growth of the small intestine or of the pancreatic islets. In one embodiment of the invention, the package contains the GLP-2 and the desired carrier, as an administration-ready formulation. Alternatively, and according to another embodiment of the invention, the package provides the GLP-2 in a form, such as a lyophilized form, suitable for reconstitution in a suitable carrier, such as buffered saline.

In one embodiment, the package is a sterile-filled vial or ampoule containing an injectable solution which comprises an effective amount of GLP-2 dissolved in an aqueous vehicle.

As an alternative to injectable formulations, the GLP-2 may be formulated for administration by other routes. Oral dosage forms, such as tablets, capsules and the like, can be formulated in accordance with standard pharmaceutical practise.

According to the present invention, the GLP-2 is administered to treat patients that would benefit from gastrointestinal tissue growth. In one aspect, patient candidates are those who would benefit from growth of small intestine tissue. The effects of GLP-2 on this tissue, as evidenced by the results exemplified herein, is dramatic and would clearly benefit those patients suffering from diseases or conditions marked by abnormalities in the small intestinal tract mucosa, which include ulcers and inflammatory disorders; congenital or acquired digestion and absorption disorders including malabsorption syndromes; and diseases and conditions caused by loss of small intestine mucosal function particularly in patients undergoing extended parenteral feeding or who, as a result of surgery, have undergone resection of the small intestine and suffer from short-gut syndrome and cul-de-sac syndrome. In general, patients who would benefit from either increased small intestinal mass and consequent increased small intestine mucosal function are candidates for treatment with GLP-2. Particular conditions that may be treated with GLP-2 include the various forms of sprue including celiac sprue which results from a toxic reaction to $\alpha$-gliadin from wheat, and is marked by a tremendous loss of villae of the small intestine; tropical sprue which results from infection and is marked by partial flattening of the villae; hypogammaglobulinemic sprue which is observed commonly in patients with common variable immunodeficiency or hypogammaglobulinemia and is marked by significant decrease in villus height. Other conditions that may be treated with GLP-2, or for which GLP-2 may be useful prophylactically, include radiation enteritis, infectious or post-infectious enteritis, regional enteritis (Crohn's disease), small intestinal damage due to toxic or other chemotherapeutic agents, and patients with short bowel syndrome.

In another aspect, patient candidates for treatment with GLP-2 are those who would benefit from growth of pancreatic islets, and particularly from proliferation or regeneration of pancreatic islets. Such patients include those suffering from diseases or conditions marked by the absence or reduction of pancreatic islets or by reduced pancreatic islet function. Particular patient candidates are those suffering from type 1 or type 2 diabetes, as well as patients with secondary forms of diabetes due to infiltration, inflammation or destruction of the pancreas.

The therapeutic dosing and regimen most appropriate for patient treatment will of course vary with the disease or condition to be treated, and according to the patient's weight and perhaps sex and age. The results presented hereinbelow demonstrate that a dose of GLP-2 equivalent to about 2.5 mg/kg over 10 days can generate very significant increases in both small intestine mass and in the number and size of pancreatic islets. It is expected that much smaller doses, in the $\mu$g/kg range and perhaps into the ng/kg range, and perhaps shorter or longer duration or frequency of treatment, will also produce therapeutically useful results, i.e., a statistically significant increase particularly in small intestine mass or in pancreatic islet size and number. The dosage sizes and dosing regimen most appropriate for human use can be determined in properly designed clinical trials.

In another of its aspects, the invention provides for the treatment of patient candidates as just identified using implanted cells that have either been conditions in vitro or in vivo by prior incubation or treatment with GLP-2, or have been engineered genetically to produce it. Conditioning of the cells ex vivo can be achieved simply by growing the cells or tissue to be transplanted in a medium that has been supplemented with a growth-promoting amount of the GLP-2 and is otherwise appropriate for culturing of those cells. The cells can, after an appropriate conditioning period, then be implanted either directly into the patient or can be encapsulated using established cell encapsulation technology, and then implanted. Alternatively, the cells to be implanted can be raised in vitro from a cell that has been engineered genetically to express or to over-express either the glucagon gene or, more directly, DNA coding solely for GLP-2. The sequence of such DNA can readily be determined from the amino acid sequence of the selected GLP-2, with the limitation that only GLP-2 forms containing genetically encoded amino acids can be produced in this manner. Various viral vectors, suitable for introduction of genetic information to human cells, can be employed and will incorporate the GLP-2 (or glucagon)-encoding DNA under expression controls functional in the host cells. Once altered genetically, the engineered cells can then be implanted using procedures established in the art.

EXAMPLES

In a first experiment designed to investigate the effect of glicentin on small bowel growth, two groups of six mice (8 week, CD1 females from Charles River Laboratories) were treated as follows. Each mouse received 41.5 $\mu$g injections every 12 hours for 10 days. The injections were delivered subcutaneously in a final volume of 16% gelatin, with 0.5 cc injected subcutaneously every 12 hours. The glicentin (rat) dissolved easily in 10 ml water. Control mice received 0.5 cc of 16% gelatin solution, but no peptide, every 12 hours. Mice were fed standard rat chow with free access to food and water, until 12 hours prior to sacrifice, at which time food was withheld, and water only was given. The weight of the small intestine was ascertained by excising the entire bowel, and removing the stomach (proximal end) and appendix/cecum/large bowel (distal end). The remaining small intestine was cleaned with saline to remove feces, and weighed. Results were follows:

|  | Weight of Mice (gm) | | Small bowel weight (gm) |
| --- | --- | --- | --- |
|  | Day 0 | Day 10 | Day 10 |
| Control | 30.0 | 27.8 | 1.6 |
|  | 29.8 | 27.5 | 1.3 |
|  | 28.7 | 25.6 | 1.7 |
|  | 28.8 | 25.8 | 1.2 |
|  | 28.0 | 25.8 | 0.7 |
|  | 27.9 | 26.2 | 1.3 |
| Glicentin | 27.9 | 26.6 | 1.6 |
|  | 27.1 | 26.2 | 1.7 |
|  | 28.0 | 26.6 | 1.3 |
|  | 24.8 | 24.5 | 1.6 |
|  | 27.2 | 24.7 | 1.7 |
|  | 26.5 | 25.8 | 1.9 |

With these results indicating that the small intestine growth-promoting effect of glicentin was modest, a second experiment using the same protocols was performed to investigate the effects of other proglucagon gene-derived products, including GLP-1 and GLP-2. For this purpose, GLP-2 of SEQ ID NO:3 and human GLP1 (7-36amide) were custom synthesized by application of the tBoc-based solid phase approach. Analysis of GLP-2, conforming to SEQ ID NO:3, revealed a purity of 95% by analytical HPLC (20 $\mu$l sample of 1.0 mg/ml; 5 $\mu$ Vydac C18 column, 0.1% TFA/ 20–60% CH$_3$CN over 20 mins at 1.5 ml/min).

GLP-2 formulations for injection were prepared as follows: Gelatin was dissolved in warm water to a weight ratio of 16%, and the 50 mL solution was autoclaved and cooled to room temperature. A peptide solution was then separately prepared by mixing 5 mg of GLP-2 with water at a volume slightly less than 10 mL, and then adding 1N acetic acid in a volume (10–20 $\mu$L) sufficient to dissolve the peptide completely. The pH was then readjusted to about 7.0 by addition of an equal volume of 1N NaOH (10–20 $\mu$L), and the solution volume was then adjusted to 10 mL by addition of distilled water. To prepare the formulation for injection, the 10 mL peptide solution and the 50 mL solution of 16% gelatin were combined with mixing, and aliquots for injection were drawn into a 0.5 mL insulin syringe. The same procedure was used to formulate the GLP-1, with the exception that no acid/base adjustment was necessary given its relative greater solubility in water.

Mice were injected with 0.5 ml of the 16% gelatin solution, without or with peptide (62.5 $\mu$g/dose). Four groups of four mice (8 week, CD1 females from Charles River Laboratories) were injected twice daily for 10 days. Results are tabulated below:

|  | Weight of Mice (gm) | | Small bowel weight | | |
| --- | --- | --- | --- | --- | --- |
|  | Day 0 | Day 10 | Day 10 (gm) | Ave | % body wt |
| Control | 26.0 | 25.4 | 1.4 | 1.4 ± .04 | 5.47 ± .14 |
|  | 27.0 | 25.9 | 1.3 |  |  |
|  | 26.0 | 26.7 | 1.5 |  |  |
|  | 25.6 | 24.4 | 1.4 |  |  |
| GLP-1 | 26.6 | 24.8 | 1.4 | 1.33 ± .04 | 5.26 ± .25 |
|  | 23.2 | 22.8 | 1.3 |  |  |
|  | 26.0 | 27.0 | 1.2 |  |  |
|  | 25.1 | 26.5 | 1.4 |  |  |
| GLP-2 | 25.2 | 23.7 | 1.8 | 2.08 ± .14 | 8.12 ± .40 |
|  | 27.1 | 25.7 | 2.3 |  |  |
|  | 28.4 | 27.1 | 2.4 |  |  |
|  | 25.8 | 25.4 | 1.8 |  |  |

These results demonstrate that, at a dose of about 2.5 mg/kg (640 nmole/kg), GLP-2 exhibits a statistically significant ($p<0.05$) increase in the mass of small intestine after twice daily treatment for 10 days, relative both to the control group receiving no peptide, and to the group receiving another glucagon-related peptide, GLP-1. Relative to the results presented here for glicentin, it is also clear that GLP-2 constitutes a major intestinal tissue growth factor.

Effects of the administration of GLP-2 to these mice was further explored, by sectioning gastrointestinal organs of the four GLP-2 treated mice and the four control mice, using paraffin embedded sections and standard histopathological techniques. Islet areas were measured by morphometric analysis. Hematoxylin and eosin-stained sections were used for quantification. Total pancreatic area and total islet area in each section were measured. The data revealed that islet area was, on average, 0.31% of the total pancreatic area in the control group. On the other hand, islets of the the GLP-2-treated group constituted 0.76% of total pancreatic area, representing an increase in islet area of more than double in the GLP-2-treated group. In addition to islet size, an increase in the number of islets was observed.

We claim:

1. A pharmaceutical composition, comprising a GLP-2, or a pharmaceutically acceptable salt thereof, and a carrier, said carrier being a pharmaceutically acceptable carrier other than saline solution.

2. The pharmaceutical composition according to claim 1, wherein the GLP-2 has the amino acid sequence:

His-Ala-Asp-Gly-Ser-Phe-Ser-Asp-Glu-Met-Asn-Thr-Ile-Leu-Asp-Asn-Leu-Ala-Thr-Arg-Asp-Phe-Ile-Asn-Trp-Leu-Ile-Gln-Thr-Lys-Ile-Thr-Asp, SEQ ID NO: 3.

3. The pharmaceutical composition according to claim 2, wherein the GLP-2 is present in an amount effective to promote the growth of small intestine tissue.

4. A method for promoting the growth of small intestine tissue in a patient in need thereof, comprising the step of administering to the patient an effective amount of a pharmaceutical composition as claimed in claim 2 to promote the growth of small intestine tissue.

5. The pharmaceutical composition according to claim 2, wherein the GLP-2 is present in an amount effective to promote the growth of pancreatic islets.

6. A method for promoting the growth of pancreatic islets in a patient in need thereof, comprising the step of administering to the patient an effective amount of a pharmaceutical composition as claimed in claim 2 to promote the growth of pancreatic islets.

7. A method for treating a patient suffering from type 1 diabetes, comprising the step of administering to the patient an effective amount of a pharmaceutical composition as claimed in claim 2 to promote the growth of pancreatic islets.

8. The pharmaceutical composition according to claim 2, wherein the GLP-2 is present in an amount effective to promote the growth of gastrointestinal tissue.

9. A method for promoting the growth of gastrointestinal tissue in a patient in need thereof, comprising the step of administering to the patient an effective amount of a pharmaceutical composition as claimed in claim 2 to promote the growth of gastrointestinal tissue.

10. The pharmaceutical composition according to claim 1, wherein the GLP-2 is present in an amount effective to promote the growth of small intestine tissue.

11. A method for promoting the growth of small intestine tissue in a patient in need thereof, comprising the step of administering to the patient an effective amount of a pharmaceutical composition as claimed in claim 1 to promote the growth of small intestine tissue.

12. The pharmaceutical composition according to claim 11, wherein the GLP-2 is present in an amount effective to promote the growth of pancreatic islets.

13. A method for promoting the growth of pancreatic islets in a patient in need thereof, comprising the step of administering to the patient an effective amount of a pharmaceutical composition as claimed in claim 1 to promote the growth of pancreatic islets.

14. A method for treating a patient suffering from type 1 diabetes, comprising the step of administering to the patient an effective amount of a pharmaceutical composition as claimed in claim 1 to promote the growth of pancreatic islets.

15. The pharmaceutical composition according to claim 1, wherein the GLP-2 is of the formula:

R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 4)

wherein:

aa1 is a neutral, polar, large and nonaromatic amino acid residue;

aa2 is a neutral and polar amino acid residue;

aa3 is a neutral amino acid residue;

aa4 is a neutral, polar, large and nonaromatic amino acid residue;

aa5 is a neutral or basic amino acid residue;

X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group.

16. The pharmaceutical composition according to claim 15, wherein the GLP-2 is present in an amount effective to promote the growth of small intestine tissue.

17. A method for promoting the growth of small intestine tissue in a patient in need thereof, comprising the step of administering to the patient an effective amount of a pharmaceutical composition as claimed in claim 15 to promote the growth of small intestine tissue.

18. The pharmaceutical composition according to claim 15, wherein the GLP-2 is present in an amount effective to promote the growth of pancreatic islets.

19. A method for promoting the growth of pancreatic islets in a patient in need thereof, comprising the step of administering to the patient an effective amount of a pharmaceutical composition as claimed in claim 15 to promote the growth of pancreatic islets.

20. A method for treating a patient suffering from type 1 diabetes, comprising the step of administering to the patient an effective amount of a pharmaceutical composition as claimed in claim 15 to promote the growth of pancreatic islets.

21. The pharmaceutical composition according to claim 15, wherein the GLP-2 is present in an amount effective to promote the growth of gastrointestinal tissue.

22. A method for promoting the growth of gastrointestinal tissue in a patient in need thereof, comprising the step of administering to the patient an effective amount of a pharmaceutical composition as claimed in claim 15 to promote the growth of gastrointestinal tissue.

23. The pharmaceutical composition according to claim 1, wherein the GLP-2 is of the formula:

R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 5)

wherein:
aa1 is Ile or Val;
aa2 is Asn or Ser;
aa3 is Ala or Thr;
aa4 is Ile or Leu;
aa5 is Gln or His;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

24. The pharmaceutical composition according to claim 23, wherein the GLP-2 is present in an amount effective to promote the growth of small intestine tissue.

25. A method for promoting the growth of small intestine tissue in a patient in need thereof, comprising the step of administering to the patient an effective amount of a pharmaceutical composition as claimed in claim 23 to promote the growth of small intestine tissue.

26. The pharmaceutical composition according to claim 23, wherein the GLP-2 is present in an amount effective to promote the growth of pancreatic islets.

27. A method for promoting the growth of pancreatic islets in a patient in need thereof, comprising the step of administering to the patient an effective amount of a pharmaceutical composition as claimed in claim 23 to promote the growth of pancreatic islets.

28. A method for treating a patient suffering from type 1 diabetes, comprising the step of administering to the patient an effective amount of a pharmaceutical composition as claimed in claim 23 to promote the growth of pancreatic islets.

29. The pharmaceutical composition according to claim 23, wherein the GLP-2 is present in an amount effective to promote the growth of gastrointestinal tissue.

30. A method for promoting the growth of gastrointestinal tissue in a patient in need thereof, comprising the step of administering to the patient an effective amount of a pharmaceutical composition as claimed in claim 23 to promote the growth of gastrointestinal tissue.

31. The pharmaceutical composition according to claim 1, wherein the GLP-2 is of the formula:

R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 6)

wherein:
aa3 is a neutral amino acid residue;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

32. The pharmaceutical composition according to claim 31, wherein the GLP-2 is present in an amount effective to promote the growth of small intestine tissue.

33. A method for promoting the growth of small intestine tissue in a patient in need thereof, comprising the step of administering to the patient an effective amount of a pharmaceutical composition as claimed in claim 31 to promote the growth of small intestine tissue.

34. The pharmaceutical composition according to claim 31, wherein the GLP-2 is present in an amount effective to promote the growth of pancreatic islets.

35. A method for promoting the growth of pancreatic islets in a patient in need thereof, comprising the step of administering to the patient an effective amount of a pharmaceutical composition as claimed in claim 31 to promote the growth of pancreatic islets.

36. A method for treating a patient suffering from type 1 diabetes, comprising the step of administering to the patient an effective amount of a pharmaceutical composition as claimed in claim 31 to promote the growth of pancreatic islets.

37. The pharmaceutical composition according to claim 31, wherein the GLP-2 is present in an amount effective to promote the growth of gastrointestinal tissue.

38. A method for promoting the growth of gastrointestinal tissue in a patient in need thereof, comprising the step of administering to the patient an effective amount of a pharmaceutical composition as claimed in claim 31 to promote the growth of gastrointestinal tissue.

39. The pharmaceutical composition according to claim 1, wherein the GLP-2 is of the formula:

R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 7)

wherein:
aa3 is Ala or Thr;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

40. The pharmaceutical composition according to claim 39, wherein the GLP-2 is present in an amount effective to promote the growth of small intestine tissue.

41. A method for promoting the growth of small intestine tissue in a patient in need thereof, comprising the step of administering to the patient an effective amount of a pharmaceutical composition as claimed in claim 39 to promote the growth of small intestine tissue.

42. The pharmaceutical composition according to claim 39, wherein the GLP-2 is present in an amount effective to promote the growth of pancreatic islets.

43. A method for promoting the growth of pancreatic islets in a patient in need thereof, comprising the step of administering to the patient an effective amount of a pharmaceutical composition as claimed in claim 39 to promote the growth of pancreatic islets.

44. A method for treating a patient suffering from type 1 diabetes, comprising the step of administering to the patient an effective amount of a pharmaceutical composition as claimed in claim 39 to promote the growth of pancreatic islets.

45. The pharmaceutical composition according to claim 39, wherein the GLP-2 is present in an amount effective to promote the growth of gastrointestinal tissue.

46. A method for promoting the growth of gastrointestinal tissue in a patient in need thereof, comprising the step of administering to the patient an effective amount of a pharmaceutical composition as claimed in claim 39 to promote the growth of gastrointestinal tissue.

47. The pharmaceutical composition according to claim 1, wherein the GLP-2 is present in an amount effective to promote the growth of gastrointestinal tissue.

48. A method for promoting the growth of gastrointestinal tissue in a patient in need thereof, comprising the step of administering to the patient an effective amount of a pharmaceutical composition as claimed in claim 1 to promote the growth of gastrointestinal tissue.

49. A pharmaceutical composition, comprising a GLP-2, or a pharmaceutically acceptable salt thereof, other than human GLP-2(1-34), and a pharmaceutically acceptable carrier.

50. The pharmaceutical composition according to claim 49, wherein the GLP-2 is present in an amount effective to promote the growth of small intestine tissue.

51. The pharmaceutical composition according to claim 49, wherein the GLP-2 is present in an amount effective to promote the growth of pancreatic islets.

52. A method for promoting the growth of pancreatic islets in a patient in need thereof, comprising the step of administering to the patient an effective amount of a pharmaceutical composition as claimed in claim 49 to promote the growth of pancreatic islets.

53. A method for treating a patient suffering from type 1 diabetes, comprising the step of administering to the patient an effective amount of a pharmaceutical composition as claimed in claim 49 to promote the growth of pancreatic islets.

54. The pharmaceutical composition according to claim 49, wherein the GLP-2 is present in an amount effective to promote the growth of gastrointestinal tissue.

55. A method for promoting the growth of gastrointestinal tissue in a patient in need thereof, comprising the step of administering to the patient an effective amount of a pharmaceutical composition as claimed in claim 49 to promote the growth of gastrointestinal tissue.

56. A pharmaceutical composition, comprising a GLP-2, or a pharmaceutically acceptable salt thereof, other than human GLP-2(1-34) or human GLP-2(1-33), and a pharmaceutically acceptable carrier.

57. The pharmaceutical composition according to claim 56, wherein the GLP-2 is present in an amount effective to promote the growth of small intestine tissue.

58. The pharmaceutical composition according to claim 56, wherein the GLP-2 is present in an amount effective to promote the growth of pancreatic islets.

59. A method for promoting the growth of pancreatic islets in a patient in need thereof, comprising the step of administering to the patient an effective amount of a pharmaceutical composition as claimed in claim 56 to promote the growth of pancreatic islets.

60. A method for treating a patient suffering from type 1 diabetes, comprising the step of administering to the patient an effective amount of a pharmaceutical composition as claimed in claim 56 to promote the growth of pancreatic islets.

61. The pharmaceutical composition according to claim 56, wherein the GLP-2 is present in an amount effective to promote the growth of gastrointestinal tissue.

62. A method for promoting the growth of gastrointestinal tissue in a patient in need thereof, comprising the step of administering to the patient an effective amount of a pharmaceutical composition as claimed in claim 56 to promote the growth of gastrointestinal tissue.

63. A method for promoting the growth of small intestine tissue in a patient in need thereof, comprising the step of administering to the patient an effective amount of a pharmaceutical composition comprising a GLP-2 or a pharmaceutically acceptable salt thereof to promote the growth of small intestine tissue.

64. A method for promoting the growth of pancreatic islets in a patient in need thereof, comprising the step of administering to the patient an effective amount of a pharmaceutical composition comprising a GLP-2 or a pharmaceutically acceptable salt thereof to promote the growth of pancreatic islets.

65. A method for treating a patient suffering from type 1 diabetes, comprising the step of administering to the patient an effective amount of a pharmaceutical comprising a GLP-2 or a pharmaceutically acceptable salt thereof to promote the growth of pancreatic islets.

66. A method for promoting the growth of gastrointestinal tissue in a patient in need thereof, comprising the step of administering to the patient an effective amount of a pharmaceutical composition comprising a GLP-2 or a pharmaceutically acceptable salt thereof to promote the growth of gastrointestinal tissue.

67. A pharmaceutical composition comprising a GLP-2, or a pharmaceutically acceptable salt thereof, wherein the GLP-2 is of the formula:

R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 4)

wherein:

aa1 is a neutral, polar, large and nonaromatic amino acid residue;

aa2 is a neutral and polar amino acid residue;

aa3 is a neutral amino acid residue;

aa4 is a neutral, polar, large and nonaromatic amino acid residue;

aa5 is a neutral or basic amino acid residue;

X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group; wherein the GLP-2 is other than human GLP-2(1-34).

68. The pharmaceutical composition according to claim 67, wherein the GLP-2 is of the formula:

R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 5)

wherein:

aa1 is Ile or Val;
aa2 is Asn or Ser;
aa3 is Ala or Thr;
aa4 is Ile or Leu;
aa5 is Gln or His;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

69. The pharmaceutical composition according to claim 68, wherein the GLP-2 is of the formula:
R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 6)
wherein:
aa3 is a neutral amino acid residue;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

70. The pharmaceutical composition according to claim 69, wherein the GLP-2 is of the formula:
R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 7)
wherein:
aa3 is Ala or Thr;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

71. A pharmaceutical composition comprising a GLP-2, or a pharmaceutically acceptable salt thereof, wherein the GLP-2 is of the formula:
R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 4)
wherein:
aa1 is a neutral, polar, large and nonaromatic amino acid residue;
aa2 is a neutral and polar amino acid residue;
aa3 is a neutral amino acid residue;
aa4 is a neutral, polar, large and nonaromatic amino acid residue;
aa5 is a neutral or basic amino acid residue;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group; wherein the GLP-2 is other than human GLP-2(1-34) or human GLP-2 (1-33).

72. The pharmaceutical composition according to claim 71, wherein the GLP-2 is of the formula:
R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 5)
wherein:
aa1 is Ile or Val;
aa2 is Asn or Ser;
aa3 is Ala or Thr;
aa4 is Ile or Leu;
aa5 is Gln or His;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

73. The pharmaceutical composition according to claim 72, wherein the GLP-2 is of the formula:
R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 6)
wherein:
aa3 is a neutral amino acid residue;
X is Arg, Lys, Arg-Lys or Lys-Lys;
Y is Arg or Arg-Arg;
m is 0 or 1;
n is 0 or 1;
R1 is H or an N-terminal blocking group; and
R2 is OH or a C-terminal blocking group.

74. The pharmaceutical composition according to claim 73, wherein the GLP-2 is of the formula:
R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 7)
wherein:
aa3 is Ala or Thr;
X is Arg, Lys, Arg-Lys or Lys-Lys;
Y is Arg or Arg or Arg-Arg;
m is 0 or 1;
n is 0 or 1;
R1 is H or an N-terminal blocking group; and
R2 is OH or a C-terminal blocking group.

75. The method according to claim 63, 64, 65, or 66, wherein the GLP-2 is of the formula:
R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 4)
wherein:
aa1 is a neutral, polar, large and nonaromatic amino acid residue;
aa2 is a neutral and polar amino acid residue;
aa3 is a neutral amino acid residue;
aa4 is a neutral, polar, large and nonaromatic amino acid residue;
aa5 is a neutral or basic amino acid residue;
X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group;

wherein the GLP-2 is other than human GLP-2(1-34).

76. The method according to claim 75, wherein the GLP-2 is of the formula:

R1-[Y]m-His-Ala-Asp-Gly-Ser-Phe-Ser-Asp-Glu-Met-Asn-Thr-aa1-Leu-Asp-aa2-Leu-Ala-aa3-Arg-Asp-Phe-Ile-Asn-Trp-Leu-aa4-aa5-Thr-Lys-Ile-Thr-Asp-[X]n-R2 (SEQ ID NO: 5)

wherein:

aa1 is Ile or Val;

aa2 is Asn or Ser;

aa3 is Ala or Thr;

aa4 is Ile or Leu;

aa5 is Gln or His;

X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group.

77. The method according to claim 76, wherein the GLP-2 is of the formula:

R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 6)

wherein:

aa3 is a neutral amino acid residue;

X is Arg, Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group.

78. The method according to claim 77, wherein the GLP-2 is of the formula:

R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 7)

wherein:

aa3 is Ala or Thr;

X is Arg or Lys, Arg-Lys or Lys-Lys;

Y is Arg or Arg-Arg;

m is 0 or 1;

n is 0 or 1;

R1 is H or an N-terminal blocking group; and

R2 is OH or a C-terminal blocking group.

79. The pharmaceutical composition according to claim 1, 2, 10, 16, 24, 12, 18, 26, 15, 23, 31, 39, 32, 40, 3, 34, 42, 5, 49, 50, 57, 51, 58, 47, 8, 54, 61, 67, 68, 69, 70, 71, 72, 73, or 74, wherein the GLP-2 is of the formula:

R1-[Y]m-His-Ala-Asp-Gly-Ser-Phe-Ser-Asp-Glu-Met-Asn-Thr-Ile-Leu-Asp-Asn-Leu-Ala-aa3-Arg-Asp-Phe-Ile-Asn-Trp-Leu-Ile-Gln-Thr-Lys-Ile-Thr-Asp-[X]n-R2 (SEQ ID NO: 7)

wherein:

aa3 is Ala or Thr;

X is Arg;

Y is Arg;

m is 0;

n is 0;

R1 is H or an N-terminal blocking group; and

R2 is OH or a C-terminal blocking group.

80. A method according to any one of claims 4, 6–7, 9, 11, 13, 14, 17, 19–20, 22, 25, 27–28, 30, 33, 35, 36, 38, 41, 43, 44, 46, 48, 52, 53, 55, 59–60 or 62–66, wherein the patient is a human patient.

\* \* \* \* \*